United States Patent [19]

Haber et al.

[11] Patent Number: 4,726,404
[45] Date of Patent: Feb. 23, 1988

[54] COMBINATION CONTAINER AND AIR REMOVAL FIXTURE FOR SIMPLIFIED FILLING OF AN IMPLANTABLE HYDRAULIC DEVICE

[75] Inventors: Terry M. Haber, Lake Forest; Clark B. Foster, El Toro, both of Calif.

[73] Assignee: Habley Medical Technology Corporation, Laguna Hills, Calif.

[21] Appl. No.: 942,221

[22] Filed: Dec. 15, 1986

[51] Int. Cl.$^4$ ................................................ B65B 3/04
[52] U.S. Cl. .............................. 141/59; 128/DIG. 25; 623/14
[58] Field of Search ........................................ 141/1–12, 141/18–27, 37–66; 623/14; 128/1 R, DIG. 25, 346, 327, 774, 780, 79

[56] References Cited

U.S. PATENT DOCUMENTS 3,111,145 11/1963 Kerns ..................................... 141/26
3,935,883 2/1976 Stach ..................................... 141/27

Primary Examiner—Houston S. Bell, Jr.
Attorney, Agent, or Firm—Morland C. Fischer

[57] ABSTRACT

A combination container and air removal fixture for easily and precisely filling an implantable hydraulic device with a continuous air-free supply of hydraulic fluid. In accordance with a preferred embodiment, the hydraulic device is an elastofluidic prosthetic sphincter and the fluid is a radio-opaque fluid. A premixed and pre-proportioned supply of hydraulic fluid is contained within each of a plurality of gas-fluid exchange chambers. A hollow occlusion cuff and at least one reservoir-actuator of the prosthetic sphincter are placed in fluid communication with respective exchange chambers. When the occlusion cuff and actuator are compressed, associated pistons are moved outwardly through the exchange chambers, whereby fluid containing entrapped air is withdrawn from the cuff and the actuator and removed to the chambers. When the pistons are moved inwardly through the exchange chambers, air-free fluid is forced from the chambers and delivered to the occlusion cuff and the actuator to replace the air that was previously withdrawn.

9 Claims, 10 Drawing Figures

COMBINATION CONTAINER AND AIR REMOVAL FIXTURE FOR SIMPLIFIED FILLING OF AN IMPLANTABLE HYDRAULIC DEVICE

BACKGROUND OF THE INVENTION

1. Field of the Invention

This invention relates to a combination container and air removal fixture for simplified filling of an implantable hydraulic device, such as, for example, an elastofluidic prosthetic sphincter, or the like with a continuous air-free supply of hydraulic fluid (e.g. such as radio-opaque fluid).

2. Prior Art

As will be recognized by those skilled in the art, hydraulic, implantable devices are commonly filled in the operating room at the time of implant using well-known bowls filled with hydraulic fluid and syringes to transfer the fluid from the bowls into the device. Entrapped air is removed from the device by repeatedly flicking the device while holding the syringe at a higher elevation then the device and drawing out a fluid-air mixture. However, this technique is awkward and sometimes not totally reliable for withdrawing all of the entrapped air from the device. As an improvement to the conventional filling technique, the implantable hydraulic device is first prefilled with an appropriate fluid and then immersed in the same fluid and sealed in a sterile package to ready the device for transfer from the package to a patient. This process is known as immersion packaging. However, immersion packaging has been known to result in certain problems and inconveniences. More particularly, because the device is prefilled, relatively deep penetration by sterilizing gases and/or radiation may not be possible, thereby reducing the overall efficiency of sterilizing procedures. In addition, a problem arises in the handling and disposing of the immersion fluid which surrounds the device. That is, after the device has been unpackaged, the physician must take the time to dispose of the excess fluid in which the device was immersed. This process if often inconvenient and results in the waste of hydraulic fluid. Moreover, care must be taken to avoid spillage, whereby to create an unsafe condition in the operating room. Consequently, the use of immersion packaging techniques has proved to be both relatively cumbersome and time consuming.

For an example of a patent relating to immersion packaging, reference may be made to U.S. Pat. No. 4,597,765 issued July 1, 1986 to William Klatt.

SUMMARY OF THE INVENTION

Briefly, and in general terms, a combination container and air removal fixture is disclosed to enable operating room personnel to relatively quickly and easily fill a hydraulic device with a continuous air-free supply of hydraulic fluid. The present invention overcomes fluid waste and inefficient sterilizing procedures that are characteristic of the conventional syringe filling and immersion packaging. In accordance with a preferred embodiment of the invention, the hydraulic fluid is a premixed solution of radio-opaque fluid, and the hydraulic device is an elastofluidic prosthetic sphincter of the type having a hollow, flexible occlusion cuff and one or more flexible fluid reservoir-actuators which provide fluid for inflating the cuff. The flow of fluid between each of the actuators and the occlusion cuff is controlled by respective normally closed check valves.

The disclosed container includes a container tray on which a plurality of gas-fluid exchange chambers are located. Each of the exchange chambers has an associated piston which is movable therethrough. The exchange chambers contain hydraulic fluid to be delivered to the hydraulic prosthetic device. A container lid, which is pivotally connected to the tray, carries the prosthetic device thereon. The occlusion cuff and the actuators of the prosthetic device are placed in fluid communication with respective fluid exchange chambers by way of fluidic tubing. The flexible occlusion cuff and actuators are initially compressed so as to drive the pistons outwardly through the exchange chambers at a time when the check valves are biased closed to the flow of hydraulic fluid from the chambers. Accordingly, a portion of the trapped air within the prosthetic device is forced out of the cuff and the actuators and into the chambers. The pistons are then manually pushed inwardly through the exchange chambers at a time when the check valves are biased open to reverse fluid flow. Accordingly, air-free fluid is forced directly from the chambers into the actuators and occlusion cuff by way of the check valves to replace the air-containing fluid that was previously withdrawn. This process of air-fluid withdrawal and air-free fluid exchange may be repeated until all of the trapped air is withdrawn from the prosthetic device and removed to the exchange cylinders and all necessary hydraulic fluid is transferred out of the cylinders and delivered to the device.

DESCRIPTION OF THE PREFERRED EMBODIMENT

Figure 1:
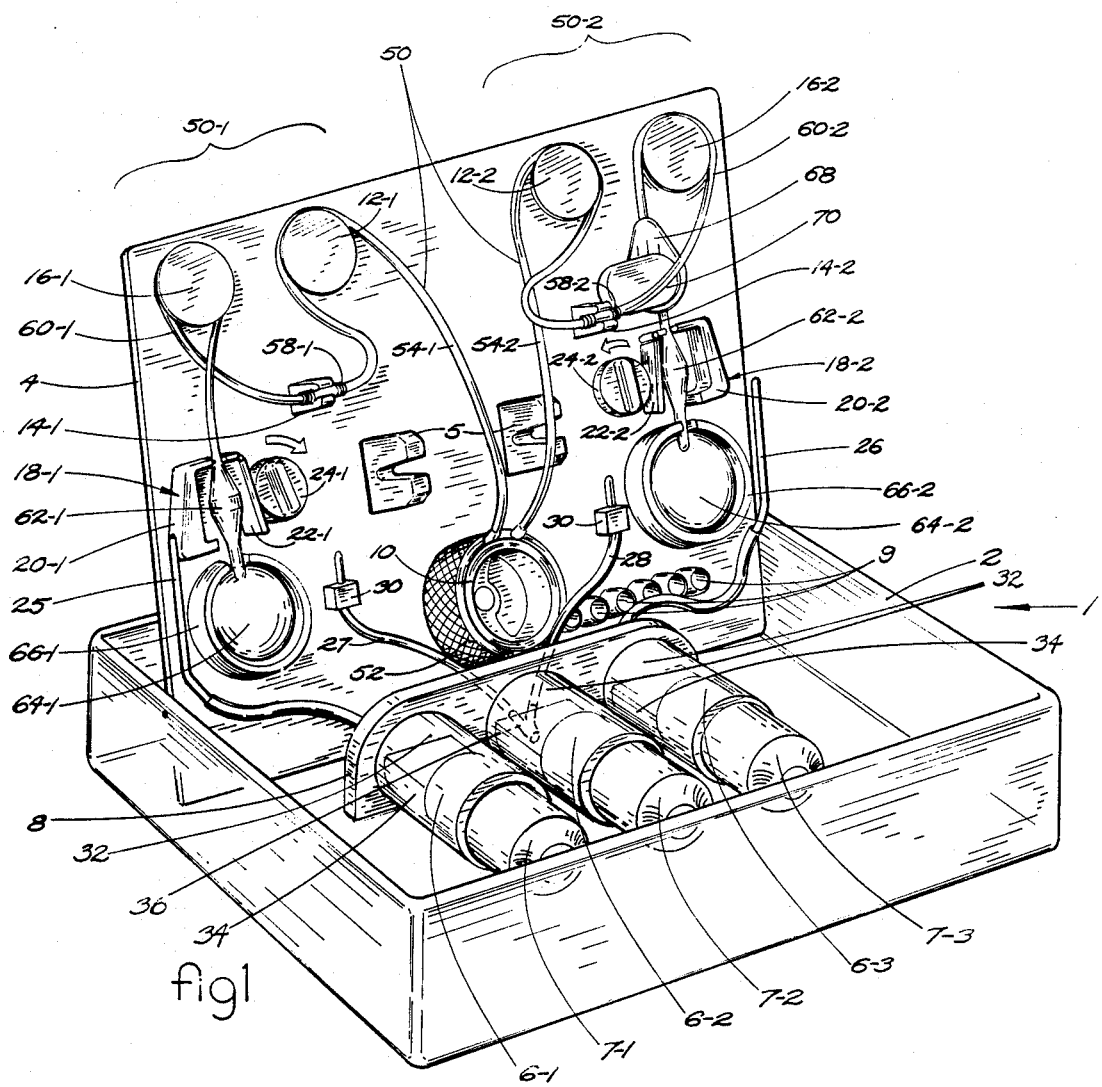
FIG. 1 is a perspective view of the combination container and air removal fixtures which form the present invention.

The combination 1 of a container and air removal fixtures for reliably and efficiently filling an implantable hydraulic device 50 with a continuous air-free supply of hydraulic fluid is best described while referring to the drawings. In FIG. 1, there is shown a rectangular container tray 2 pivotally interconnected with a container lid 4 so that the lid can be rotated to either an open position (as shown) at which to fill the device or to a closed position in order to form a compact container for convenient transport and storage. A brace 5 is affected to and extends outwardly from the lid 4. Brace 5 is dimensioned to engage the bottom of the tray 2 and thereby protect the device against possible puncture damage when the lid 4 is rotated to the closed position (not shown) above tray 2. A plurality of space connectors 9 are mounted upon the lid 4 to provide the physician-surgeon with a readily available supply should additional connectors be needed during and/or after the soon-to-be described filling procedure.

A plurality of (e.g. three) gas-fluid exchange chambers 6-1, 6-2 and 6-3 are supported by a bracket 8 which extends upwardly from the bottom of tray 2 to form the air removal fixture. Each of the exchange chambers contains an air pocket 32 lying above a premeasured, pre-proportioned supply of hydraulic (e.g. radio-opaque) fluid 34. The hydraulic device 50 is removably attached to the lid 4 and adapted to be connected, in the operating room, to the fluid exchange chambers 6-1, 6-2 and 6-3 so that fluid may be pumped, by means of associated pistons 7-1, 7-2 and 7-3, directly from the chambers into the device. In this manner, the device can be filled with a continuous supply of fluid which is devoid of undesirable air bubbles. By way of example only, and not intended as a limitation of the present invention, the implantable hydraulic device 50 attached to lid 4 is an elastofluidic, prosthetic sphincter. By way of further example, a suitable prosthetic sphincter is that described in U.S. patent application Ser. No. 752,137 filed July 5, 1985, now U.S. Pat. No. 4,634,443 the teachings of which application are incorporated herein by this reference. However, it is to be understood that the hydraulic device, itself, forms no part of the present invention.

The hydraulic prosthesis 50 is supported upon the lid 4 in a manner that will avoid kinking of fluid tubing and permit relatively quick and simplified filling and pre-implant testing. More particularly, an occlusion cuff 52, common to most prosthetic sphincters, is supported by a flexible mounting stem 10. Occlusion cuff 52 includes a hollow, expandable chamber (not shown) in which to receive fluid to thereby inflate the cuff. The hydraulic prosthesis 50 of the present invention includes first and second fluid circuits 50-1 and 50-2 which communicate with the hollow chamber of cuff 52 by way of respective first tubing sections 54-1 and 54-2. The first fluid circuit 50-1 is designated the patient controlled path and the second fluid circuit 50-2 is designated the physican controlled path. Details regarding the purpose and function of the patient and physician controlled paths 50-1 and 50-2 are found in the aforementioned patent application Ser. No. 752,137 now U.S. Pat. No. 4,634,443.

Each of the first tubing sections 54-1 and 54-2 extends upwardly from occlusion cuff 52, around a respective tubing support 12-1 and 12-2, to a tube connector 58-1 and 58-2. The tube connectors 58-1 and 58-2 are received within and removably attached to lid 4 by means of respective receptacles 14-1 and 14-2. Interconnected with the first tubing sections 54-1 and 54-2 at the tube connectors 58-1 and 58-2 are second tubing sections 60-1 and 60-2. Each of the second tubing sections 60-1 and 60-2 extends from the connection at first tubing sections 54-1 and 54-2, around a respective tubing support 16-1 and 16-2, to a normally closed check valve 62-1 and 62-2.

Connected within the second tubing section 60-2 of the physician controlled path 50-2, between tubing connector 58-2 and check valve 62-2, is a hollow physician control port 68. Physician control port 68 permits the physician-surgeon to program the baseline pressure of the occlusion cuff 52 after the hydraulic prosthesis 50 is implanted within the patient and for a period of six to eight weeks thereafter. The port 68 is retained adjacent to lid 4 by a support 70, which support prevents the port from annurizing as a consequence of relatively high pressures generated during the filling procedure. Details of the structure and advantage of the physician actuated port 68 is also available in the aforementioned patent application Ser. No. 752,137.

Surrounding the check valves 62-1 and 62-2 are respective check valve control assemblies 18-1 and 18-2. Each control assembly 18-1 and 18-2 comprises a fixed first end member 20-1 and 20-2 which is securely connected to lid 4 at one side of a check valve 62-1 and 62-2 and an articulating second end member 22-1 and 22-2 which is pivotally connected to lid 4 at the opposite side of a check valve so as to be adapted for rotational movement relative to fixed end member 20-1 and 20-2. Located adjacent each of the articulating end members 22-1 and 22-2 of the check valve control assemblies 18-1 and 18-2 is a respective cam wheel 24-1 and 24-2. During the filling operation, the details of which will be disclosed in greater detail hereinafter, the cam wheels 24-1 and 24-2 are rotated (in the direction indicated by the associated reference arrows), whereby to periodically engage and pivot the articulating control members 22-1 and 22-2 towards the fixed control members 20-1 and 20-2. During a complete rotation of the cam wheels 24-1 and 24-2, the distance between the articulating and fixed end members of check value control assemblies 18-1 and 18-2 is varied, such that the end members cooperate to relax and then compresses the check valves 62-1 and 62-2 located therebetween to achieve an advantage which will also be described in greater detail hereinafter.

Each of the check valves 62-1 and 62-2 is connected between a second tubing section 60-1 and 60-2 and a manually operated, hemispheric reservoir-actuator 64-1 and 64-2. Actuators 64-1 and 64-2 are surrounded by a respective locator ring 66-1 and 66-2 which stabilize the actuators and enable the physician to palpate the actuators of the patient and physician controlled fluid paths 50-1 and 50-2 when the hydraulic prosthesis 50 is being filled with hydraulic fluid. Subsequent to the implantation and actuation, the patient and/or physician may selectively activate one or both actuators 64-1 and 64-2 to transfer fluid for inflating the aforementioned occlusion cuff 52 of an implanted prosthesis.

Filling tubes 25 and 26 are connected at proximal ends thereof to respective gas-fluid exchange chambers 6-1 and 6-3 at submerged orifices which are isolated from air pockets 32. A pair of filling tubes 27 and 28 are connected at proximal ends thereof to the other exchange chamber 6-2 at a submerged, isolated orifice by way of a Y-shaped coupling 36. Support blocks 30 are affixed to the lid 4 for receiving and supporting at least some of the filling tubes (e.g. 28) so that fluidic connections may be easily and reliably made between the tubing sections of hydraulic prosthesis 50 and the filling tubes of the exchange chambers 6-1, 6-2 and 6-3.

Figure 2:
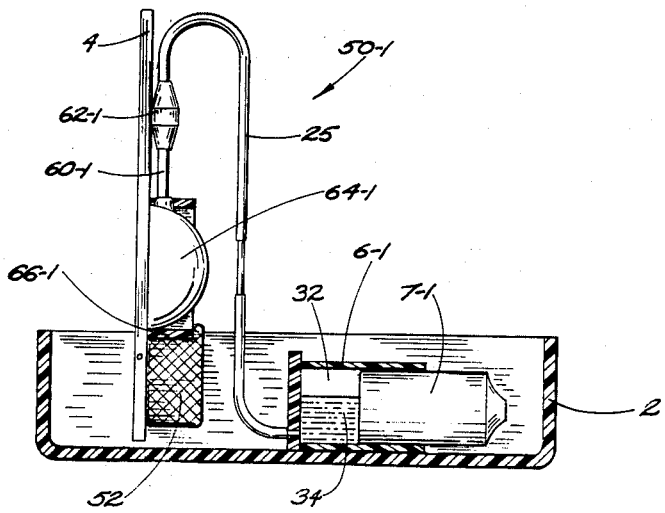
FIG. 2 is a side view of the combination of FIG. 1.
Figure 9:
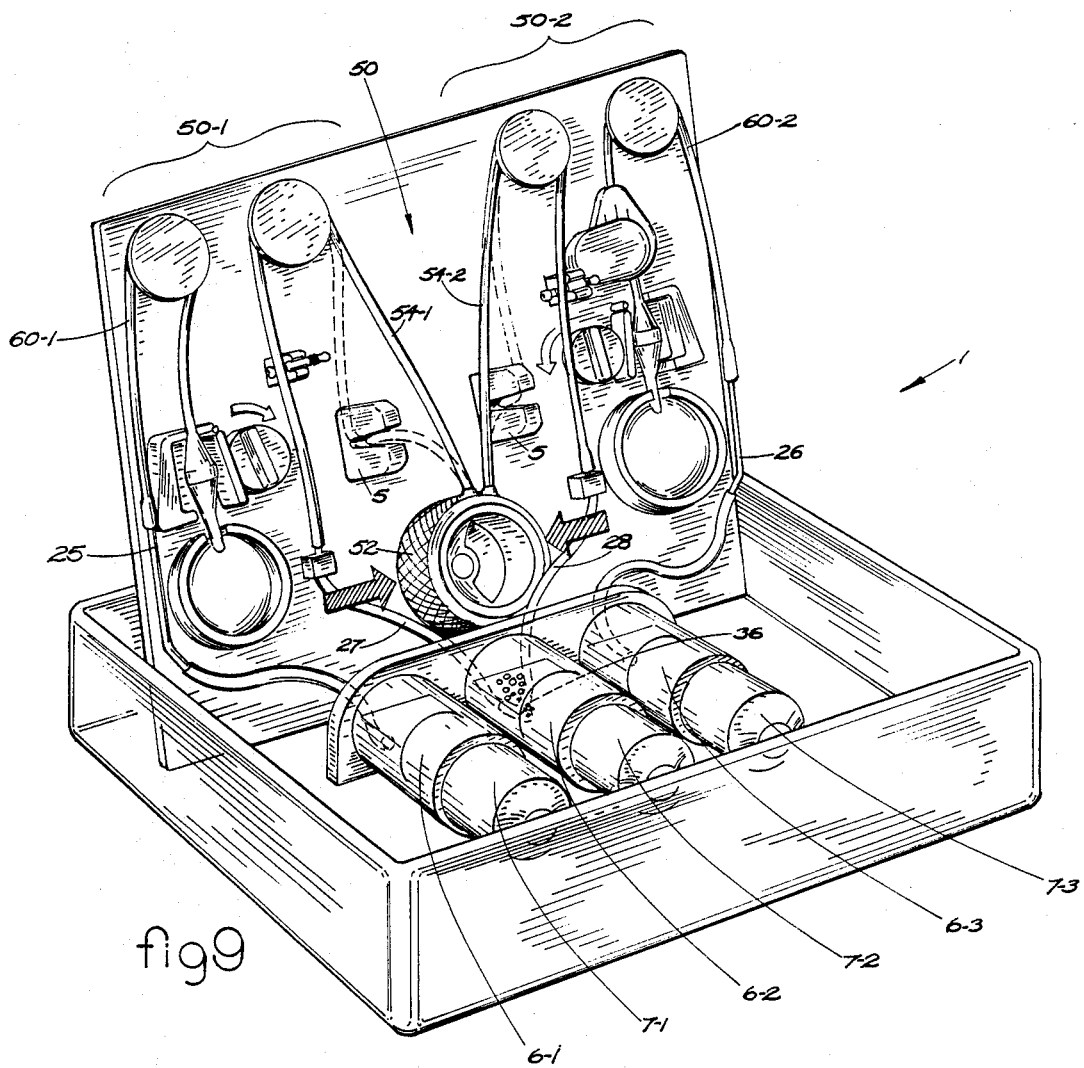
FIGS. 9-10 illustrate the steps for operating the air removal fixture of FIG. 1 for simplified filling of an occlusion cuff of the prosthetic sphincter.

More particularly, and referring concurrently to FIGS. 1 and 2 of the drawings, the reservoir-actuators 64-1 and 64-2 of hydraulic prosthesis 50 are filled with a continuous air-free supply of fluid by first connecting the fluid exchange chambers 6-1, 6-2 and 6-3 in fluid communication with the first and second tubing sections of the hydraulic prosthesis by way of filling tubes 25-28. That is to say, the first and second tubing sections 54-1, 54-2 and 60-1, 60-2 of the prosthesis 50 are released from their respective tube connectors 58-1 and 58-2. A proximal end of second tubing section 60-1 is then coupled to the distal end of filling tube 25, so that a fluid path is established between fluid exchange chamber 6-1 and the actuator 64-1 which forms the patient controlled fluid path 50-1. A proximal end of second tubing section 60-2 is correspondingly coupled to the distal end of filling tube 26, so that a fluid path is established between fluid exchange chamber 6-3 and the actuator 64-2 which forms the physician controlled fluid path 50-2. A proximal end of first tubing section 54-1 is coupled to the distal end of filling tube 27, so that a fluid path is established between fluid exchange chamber 6-2 and the occlusion cuff 52. Likewise, a proximal end of first tubing section 54-2 is coupled to the distal end of filling tube 28, so that another fluid path is established between fluid exchange chamber 6-2 and occlusion cuff 52. The fluid connection of the hydraulic prosthesis 50 with the fluid exchange chambers 6-1, 6-2 and 6-3 for withdrawing air from and filling the actuators 64-1 and 64-2 and the occlusion cuff 52 is best illustrated in FIG. 9 of the drawings.

Figure 3:
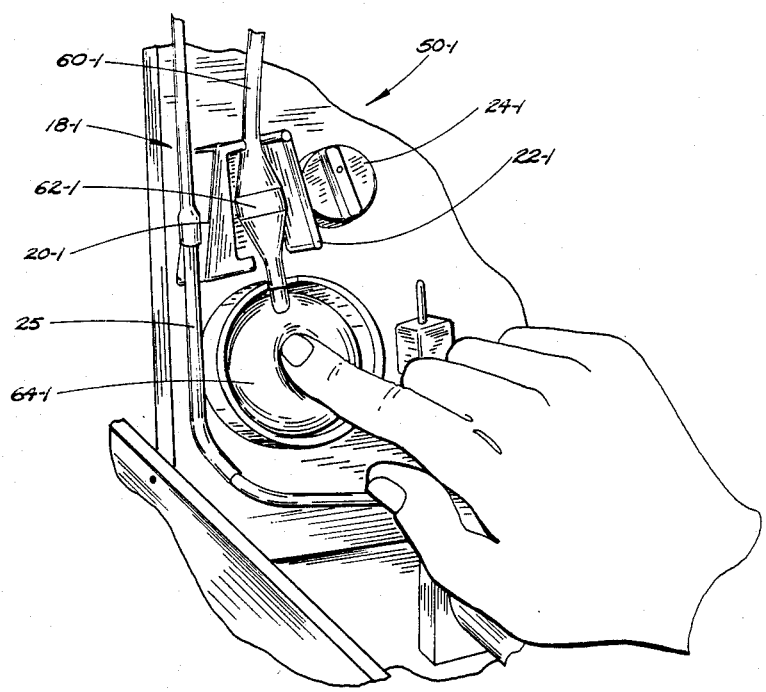
FIGS. 3-8 illustrates the steps for operating the air removal fixture of FIG. 1 for simplified filling of one or more fluid reservoir-actuators of a prosthetic sphincter.
Figure 4:
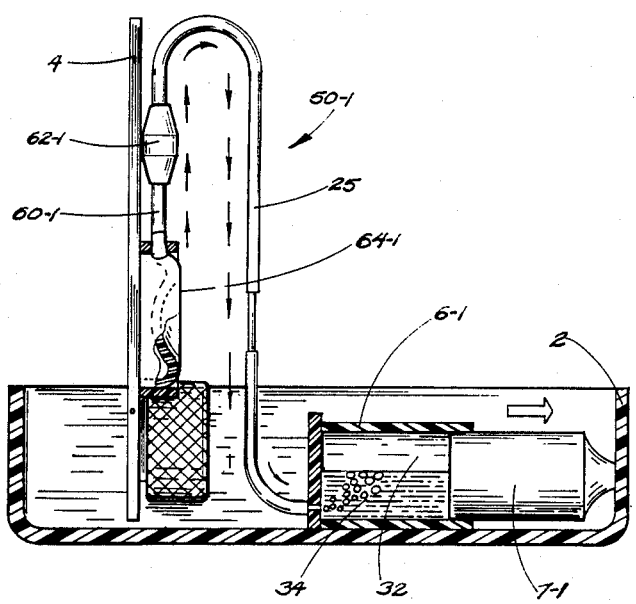

The operation of the presently disclosed apparatus and fluid exchange chambers for filling the actuators and occlusion cuff of hydraulic prosthesis 50 is now described while referring initially to FIGS. 3 and 4 of the drawings. Although specific reference is made to only elements of the patient controlled fluid path 50-1, it is to be understood that the physician controlled fluid path 50-2 is filled in an identical manner to that disclosed below. The physician rotates cam wheel 24-1 so as to permit the articulating end member 22-1 of check valve control assembly 18-1 to pivot away from the fixed end member 20-1, provided that end member 22-1 has not already been pivoted. The spaced disposition of control members 20-1 and 22-1 causes check valve 62-1 to be relaxed and thereby closed to hydraulic fluid flow therepast in a direction from chamber 6-1 to actuator 64-1.

The physician then depresses the hemispheric body of actuator 64-1, whereby air, which occupies the enclosed volume of actuator 64-1 during prosthesis manufacture, creates a pressure head to open the normally closed check valve 62-1. Hence, air filled fluid is forced out of actuator 64-1 and into the fluid exchange chamber 6-1 (in the direction of the arrows of FIG. 4) by way of tubing section 60-1 and filling tube 25. The resulting flow into the exchange chamber 6-1 drives the associated piston 7-1 in a direction outwardly therethrough. Accordingly, the air pocket 32 of chamber 6-1 is now filled with an increased volume of air lying above a relatively heavier supply of hydraulic fluid 34.

Figure 5:
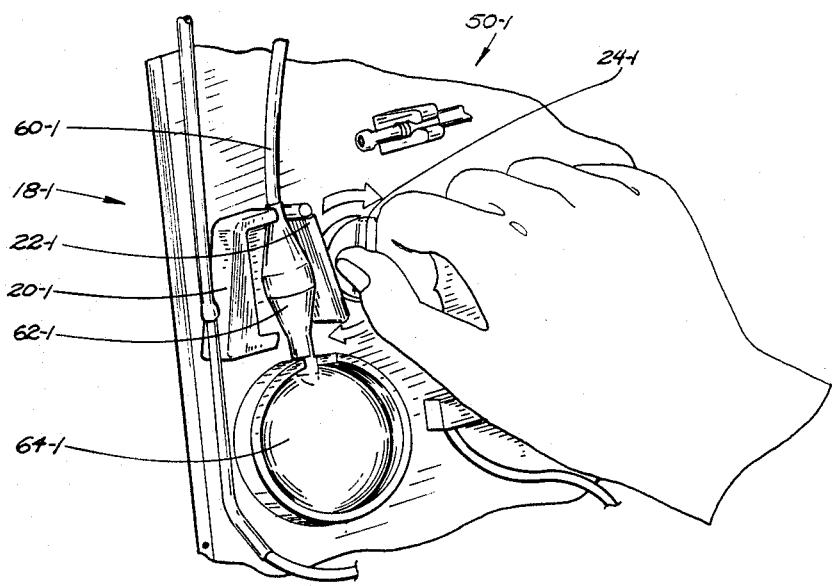
Figure 6:
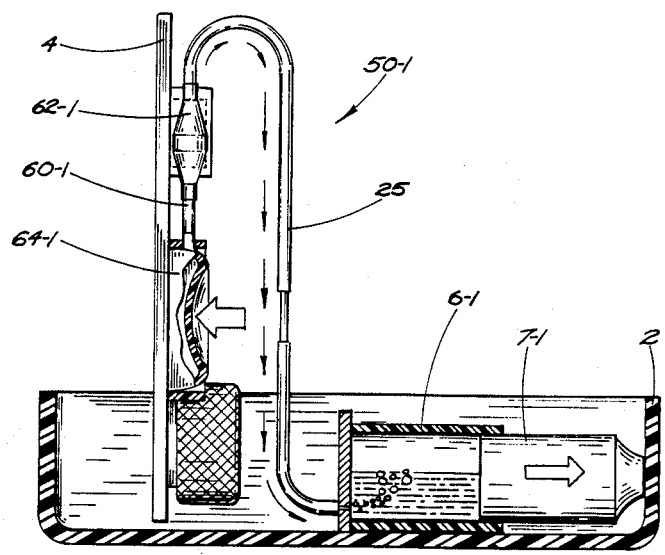

Referring now to FIGS. 5 and 6 of the drawings, the physician rotates cam wheel 24-1 (in the direction of the reference arrow of FIG. 5) so as to pivot the articulating end member 22-1 of check valve control assembly 18-1 towards fixed end member 20-1 and into engagement with check valve 62-1. The adjacent disposition of the fixed and articulating end members 20-1 and 22-1 causes normally closed check valve 62-1 to be compressed or squeezed therebetween and thereby locked in an open configuration to permit fluid flow therepast in a direction from exchange chamber 6-1 to actuator 64-1, or visa versa.

Figure 7:
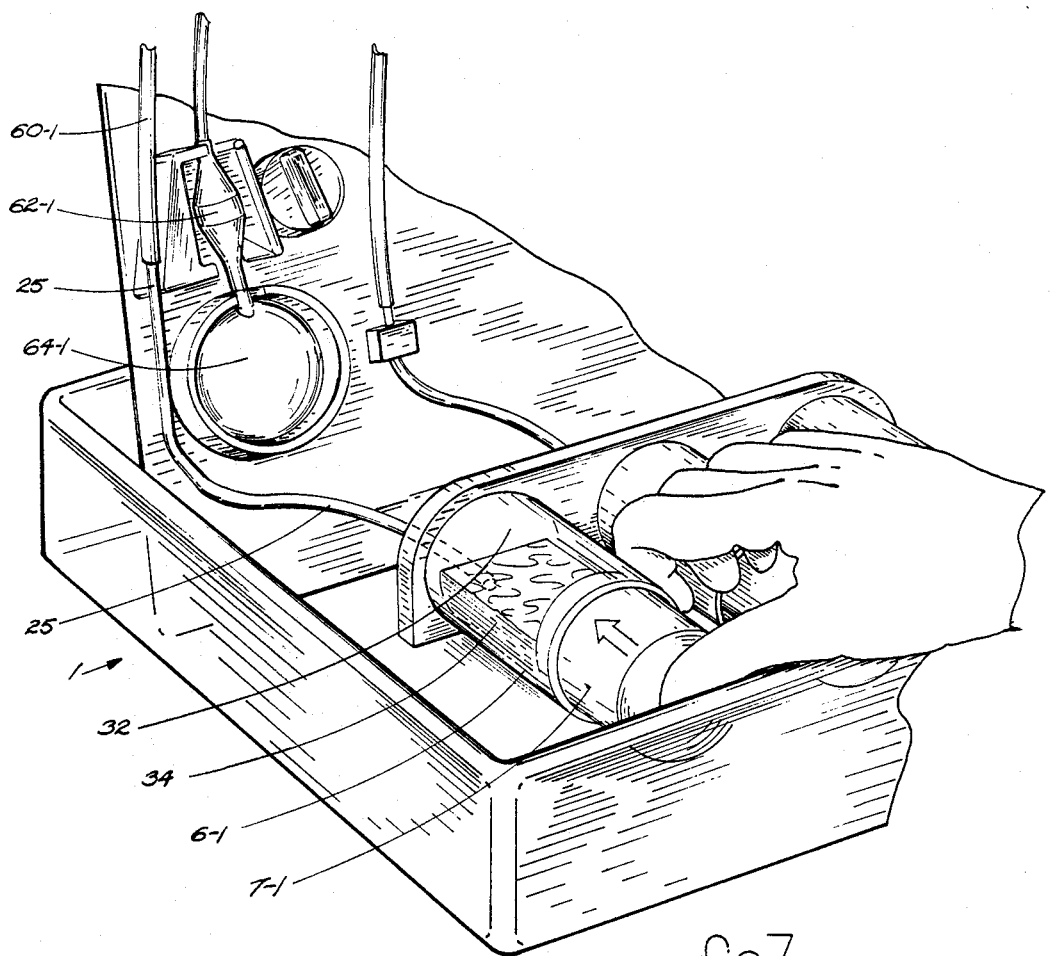
Figure 8:
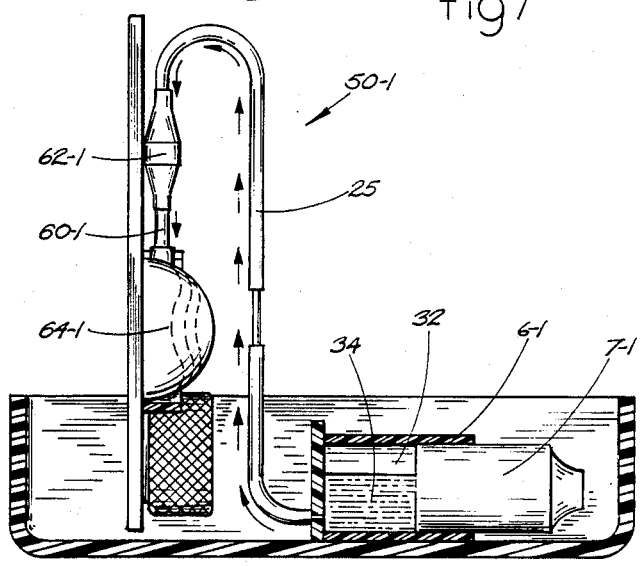

In FIGS. 7 and 8 of the drawings, the physician manually pushes the piston 7-1 in a direction inwardly through fluid exchange chamber 6-1 to force hydraulic fluid 34 directly from the chamber 6-1 to the actuator 64-1 by way of a fluid path comprising fluid tube 25, open check valve 62-1 and tubing section 60-1. Because the supply of fluid 34 in exchange chamber 6-1 lies below the air pocket 32, only air-free fluid will be infused from chamber 6-1 to filling tube 25 when piston 7-1 is pushed through the chamber. Hence, the actuator 64 is filled with air-free fluid to replace the air-filled fluid that was previously forced out when the actuator was depressed.

Figure 10:
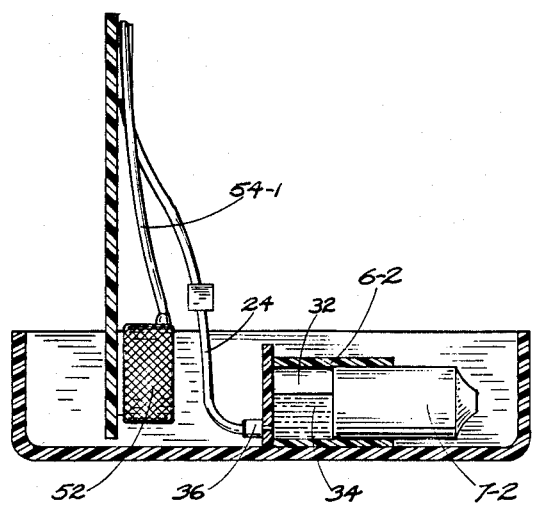

The operation of the apparatus 1 for filling the occlusion cuff 52 of the hydraulic prosthesis 50 is described while referring to FIGS. 9 and 10 of the drawings. The physician-surgeon first compresses or squeezes the occlusion cuff 52 (as indicated by the shaded arrows in FIG. 9). Air which is trapped within the occlusion cuff 52 during manufacture of the prosthesis 50 is thereby forced from the cuff and into fluid exchange chamber 6-2 by way of the aforementioned submerged orifice, Y-coupling 36 and parallel fluid paths comprising the first tubing sections and filling tubes 54-1, 27 and 54-2, 28. The resulting air flow into exchange chamber 6-2 bubbles upwardly into the air pocket 32 from the fluid supply 34 therebelow to drive the associated piston 7-2 outwardly therefrom. Accordingly, the air pocket 32 of exchange chamber 6-2 is filled with an increased volume of air which lies above the premeasured and preproportioned supply of hydraulic fluid 34.

Next, the physician manually pushes the piston 7-2 into and through the fluid exchange chamber 6-2 to force hydraulic fluid 34 directly from the chamber into occlusion cuff 52 to replace the air that was previously withdrawn. The process of gas-entrapped fluid withdrawal and gas-free fluid infusion may be repeated until all of the trapped air is removed from occlusion cuff 52 to fluid exchange chamber 6-2 and hydraulic fluid is transferred from the chamber to the cuff.

The foregoing procedure of gas entrapped fluid withdrawal and gas-free fluid infusion is repeated until all of the trapped air is removed and hydraulic fluid has been transferred from the fluid exchange chambers 6-1 and 6-2 to the fluid path 50-1, such that the occlusion cuff 52 is filled, but not inflated, and the actuator 60-1 has regained its as-molded hemispheric configuration. By using transparent tubing, the physician-surgeon may visually ascertain when all of the air bubbles have been removed from the hydraulic prosthesis 50. When the physician is certain that the prosthesis 50 is free of air, he disconnects the prosthesis from the exchange chambers and reconnects the first and second tubing sections 54-1 to 60-1 and 54-2 to 60-2 to achieve the prosthesis configuration illustrated in FIG. 1. The hydraulic prosthesis 50 is now ready for pre-implant testing for proper function by depressing actuators 64-1 and 64-2 and inflating occlusion cuff 52 to increase the occlusive pressure generated thereby. After testing has been successfully completed, the prosthesis 50 may be removed from the lid 4 of the container and implanted within the body of the patent by means of conventional surgical techniques.

By virtue of the present invention, a compact package is available by which an operating room physician-surgeon can quickly and simply fill an implantable hydraulic prosthetic device with a continuous air-free supply of hydraulic fluid. Since the prosthetic device may be manufactured free of fluid, sterilizing gases and/or radiation may penetrate more deeply than that possible when the conventional bowl-syringe or more recent immersion packaging techniques are utilized. Also, because a predetermined volume of hydraulic fluid is packaged within the fluid exchange chambers, fluid waste is minimized when compared with the waste and disposal requirements commonly associated with conventional filling techniques. What is more, the present apparatus provides for enhanced sterility in the operating room, inasmuch as a precise volume of premixed, prepackaged hydraulic fluid may be infused directly from the fluid exchange chambers to the prosthesis without exposure to a non-sterile environment or to non-sterile air.

It will be apparent that while a preferred embodiment of the invention has been shown and described, various modifications and changes may be made without departing from the true spirit and scope of the invention. By way of example, although the implantable hydraulic prosthesis has been described herein as a prosthetic sphincter, it is to be understood that the advantages of the present invention are also applicable to other implantable hydraulic devices, such as, but not limited to, a penile implant, a testicular prosthesis, an esophageal cuff, and the like. Moreover, while the prosthetic sphincter herein has been described as having patient and physician controlled fluid paths which communicate with an inflatable occlusion cuff, it is also to be understood that this invention is not limited to filling an implantable hydraulic device having multiple fluid paths. The apparatus of this invention may be used for filling devices having any suitable number of fluid paths by merely selecting a corresponding number of fluid exchange chambers.

Having thus set forth a preferred embodiment of the present invention, What is claimed is:

1. Apparatus for removing entrapped air from and filling a hydraulic device with hydraulic fluid, said hydraulic device including a hollow, flexible actuator to be filled with a supply of air-free hydraulic fluid and a check valve to control the flow of hydraulic fluid to the actuator, said apparatus comprising:
   at least one fluid exchange chamber containing the hydraulic fluid with which to fill said actuator, said chamber having a piston movable therethrough;
   means to control the bias of said check valve so that said check valve is either open or closed to the flow of hydraulic fluid therepast; and
   means to place said fluid exchange chamber in fluid communication with the actuator of said hydraulic device, such that a compression of said flexible actuator with said control means closing said check valve to hydraulic fluid flow moves said piston in a direction outwardly from said chamber and causes air to be withdrawn from said actuator and removed to said chamber; and
   moving said piston in a direction inwardly through said fluid exchange chamber with said control means opening said check valve to hydraulic fluid flow forces hydraulic fluid in said chamber to be delivered to said actuator for replacing the air that is withdrawn therefrom.

2. The apparatus recited in claim 1, wherein said hydraulic device is an implantable prosthetic device.

3. The apparatus recited in claim 2, wherein said prosthetic device is a prosthetic sphincter.

4. The apparatus recited in claim 3, wherein said prosthetic sphincter also includes a hollow, flexible occlusion cuff to be filled with a supply of hydraulic fluid, said apparatus further comprising:
   at least a second fluid exchange chamber containing the hydraulic fluid with which to fill said occlusion cuff, said chamber having a piston movable therethrough; and
   means to place said second fluid exchange chamber in fluid communication with said occlusion cuff, such that a compression of said flexible occlusion cuff moves said piston in a direction outwardly from said second chamber and causes air to be withdrawn from said cuff and removed to said second chamber; and
   moving said piston in a direction inwardly through said second fluid exchange chamber forces hydraulic fluid in said chamber to be delivered to said occlusion cuff for replacing the air that is withdrawn therefrom.

5. The apparatus recited in claim 1, wherein said check valve control means includes first and second end members spaced from one another at opposite sides of said check valve;
   said apparatus further comprising means to vary the spacing between said first and second end members.

6. The apparatus recited in claim 5, wherein one of said control means and members has a fixed position relative to said check valve and the opposite end member is movable relative to said fixed end member for varying the spacing between said first and second end members.

7. The apparatus recited in claim 6, wherein said means to vary the spacing between the first and second end members of said check valve control means includes a cam wheel located adjacent said movable end member, said cam wheel being rotated to a first position at which to increase the spacing between said first and second end members for closing said check valve to the flow of hydraulic fluid therepast or said cam wheel being rotated to a second position for moving said movable end member toward said fixed end member and compressing said check valve therebetween for opening said check valve to the flow of hydraulic fluid therepast.

8. The apparatus recited in claim 1, further comprising a tray in which said fluid exchange chamber is located and a lid for supporting said hydraulic device, said tray and lid being pivotally interconnected so that said lid may be rotated to either a closed or open position relative to said tray.

9. Apparatus for removing air from and filling a hydraulic prosthetic sphincter, said sphincter including a hollow flexible actuator to be filled with a supply of air free hydraulic fluid, a check valve to control the flow of hydraulic fluid to the actuator, and a hollow, flexible occlusion cuff also to be filled with a supply of air free hydraulic fluid;
   said air removal and fluid filling apparatus comprising first and second fluid chambers containing supplies of air free hydraulic fluid with which to fill said actuator and said occlusion cuff and having respective pistons movable therethrough, and means to place said first and second fluid chambers in fluid communication with said actuator and said occlusion cuff, respectively;
   said air removal and fluid filling apparatus further comprising means to control the bias of said check valve so that said check valve is either open or closed to the flow of hydraulic fluid therepast;
   a compression of said actuator and said occlusion cuff with said check valve biased closed to hydraulic fluid flow therepast causing the corresponding movement of said pistons in a direction outwardly from said first and second fluid chambers for causing air and air filled fluid to be withdrawn from said actuator and cuff and removed to said chambers; and
   the movement of said pistons in a direction inwardly through said first and second fluid chambers with said check valve biased open to hydraulic fluid flow therepast forcing air free hydraulic fluid in said chambers to be delivered to said actuator and cuff for replacing the air and air filled fluid that is withdrawn therefrom.

* * * * *